United States Patent
Ghigini

[11] 4,044,615
[45] Aug. 30, 1977

[54] ELECTRIC SPHYGMOMANOMETER

[76] Inventor: Rino Ghigini, c/o Dr. Ing. Misitano A.G., Via Padova, 217, 20127 Milan, Italy

[21] Appl. No.: 636,672

[22] Filed: Dec. 1, 1975

[51] Int. Cl.² .......................... G01L 19/08; G01L 7/06
[52] U.S. Cl. ........................................ 73/391; 73/410; 128/2.05 Q
[58] Field of Search ................... 128/2.05 Q, 2.05 M, 128/2.05 A; 73/410, 402, 391; 346/33 M, 102

[56] References Cited

U.S. PATENT DOCUMENTS 3,754,545  8/1973  Weinstein ............................ 346/102
3,867,926  2/1975  Friedlander ..................... 128/2.05 Q Primary Examiner—Donald O. Woodiel

[57] ABSTRACT

In a sphygmomanometer apparatus the invention provides a blood pressure recording paper disc presenting a printed blood pressure graduation and associated to a platform to be swung by the blood pressure impulses. The platform is connected to a sphygmomanometer bellow device through an adjustable device including a conical pulley and a wire connected by a side to the bottom of the bellow body and at the opposite and to a bush to be adjustably fixed to the spindle carrying platform.

1 Claim, 6 Drawing Figures

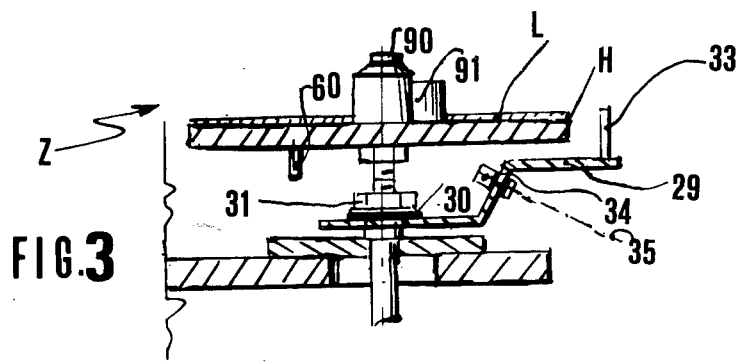
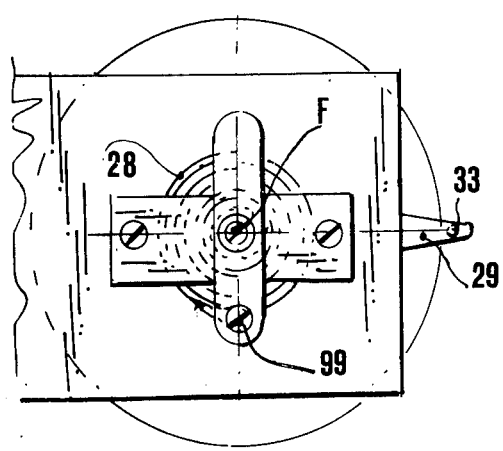
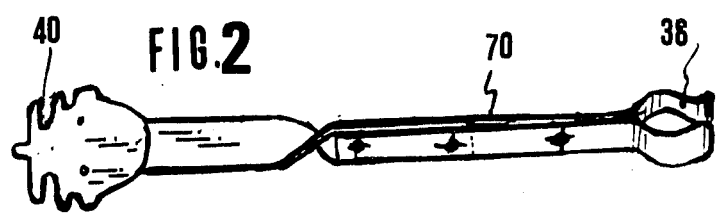

ELECTRIC SPHYGMOMANOMETER

DESCRIPTION OF PRIOR ART

Known sphygmomanometers generally suffer from the drawback that they do not provide a blood pressure measurement that may be easily kept as record for future uses or check purpose. Moreover their construction is rather complicated and therefore expensive.

BACKGROUND OF THE INVENTION

My invention aims to provide a blood pressure record under the form of a paper disc that may be easily read whereby it may be a source of absolutely objective records and at the same time it may easily kept for successive recording or checking purposes. Accordingly my invention provides in a blood pressure recording device including a manometric bracelet or cuff adapted to encircle a limb of a person: a pressure means for applying a pressure to said limb; a rotatable platform for removably supporting a blood pressure record disc and rotating the disc in response to the value of pressure applied by said pressure means; a writing instruments for writing on said record disc and actuating means for operating said writing means to write on said record disc in response to pulse beats of blood pressure; and means for locating the said record disc with respect to the said rotatable platform, the improvement comprising the provision of a mechanism for rotating the said platform including: a cylindrical bellows having a bottom and a flanged opening; a rigid cup shaped body surrounding the said bellows; a flanged rigidly connected with the said cup shaped body and sealing the said flanged opening of the bellows to define a sealed chamber in communication with the said cuff; a first screw setting means screwed to said flanged frame; a strong cylindrical spring arranged in the said bellows and compressed between the said bottom of the said bellows and the said first screw setting means; a rotatable spindle connected to said platform; a conical pulley adjustably connected to the said spindle so as to provide a second setting means; a bush adjustably connected to said rotatable spindle; a wire connected at one end to said bottom of the bellows and at the other end to the said conical pulley whereby the axial deformations of the said bellows in response to decreasing pressure in the said cuff may be adjustably converted into rotation of the said conical pulley and of the said platform; adjustable elastic means for biasing the said platform in a direction opposite to that caused by the strong cylindrical spring and constituting a third setting means.

Other objects and advantageous features of the invention will be apparent from the description and claims.

BRIEF DESCRIPTION OF THE DRAWING

The nature and characteristic features of the invention will be more readily understood from the following description taken in conjunction with the accompanying drawings forming part thereof, in which:

FIG. 2 is a perspective view of the arm carrying the writing instrument;

FIG. 3 is an enlarged view of the detail Z of FIG. 1;

FIG. 4 is a partial bottom view showing a spring biasing the platform carrying spindle, the said platform receiving the paper record disc;

FIG. 6 is an enlarged fragmentary elevational view of the writing instrument to be engaged by the fork shaped arm shown in the FIG. 2.

DETAILED DESCRIPTION OF THE INVENTION

Figure 1:
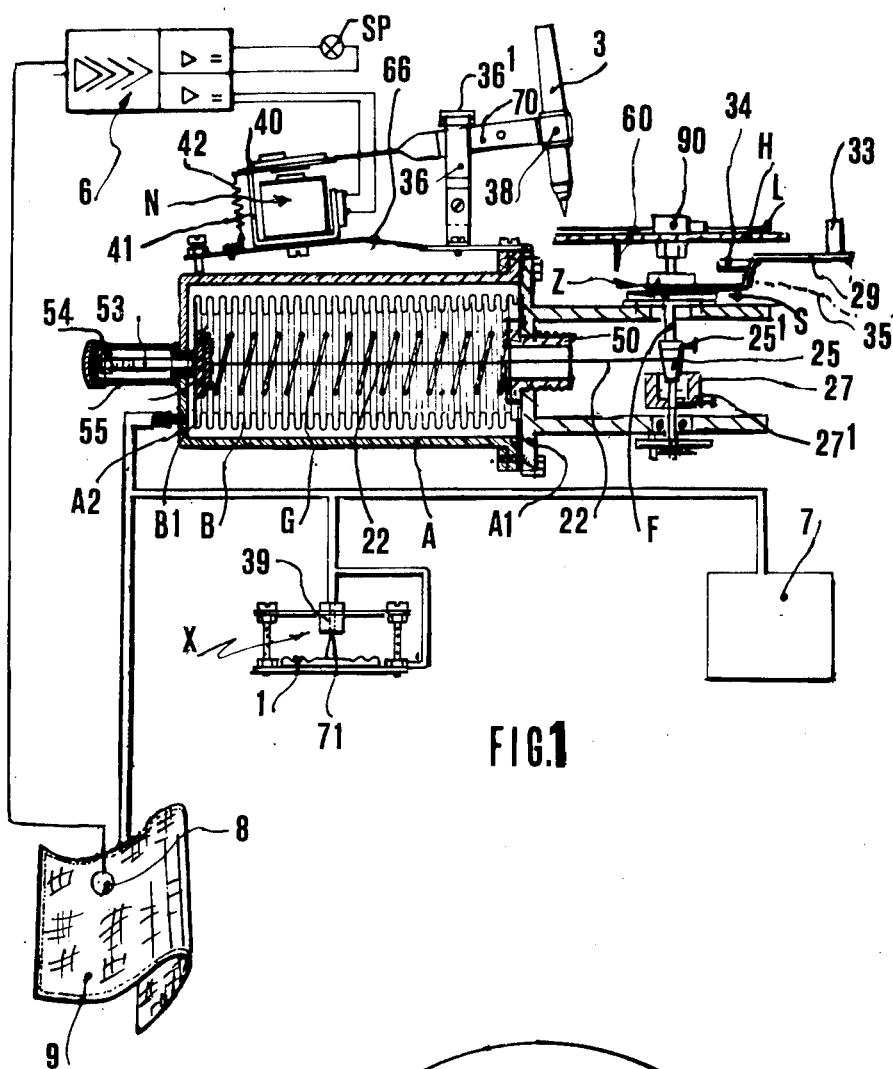
FIG. 1 is a diagram showing the operation of the invention.
Figure 5:
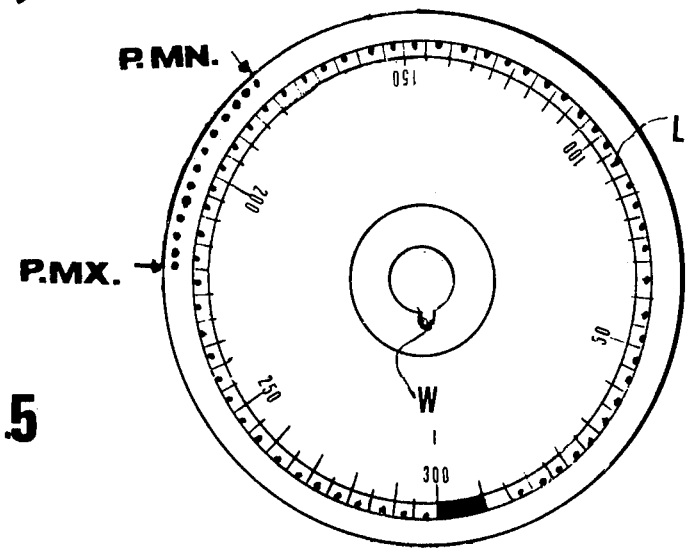
FIG. 5 is a top view of the blood pressure record paper disc.

The description for grounds of clarity and consistency will follow under the following five headings:
 I Elastic bellows and amplifying wire-pulley mechanism (FIG. 1).
 II Spring biasing of the paper disc carrying platform and limitation of the maximal blood pressure to be measured (FIGS. 1, 3, 4).
 III Writing instrument control (FIGS. 1, 2, 6).
 IV Automatic control of the decompression (FIG. 1).
 V Operation (FIGS. 1, 5).

I ELASTIC BELLOWS AND AMPLIFYING WIRE-PULLEY MECHANISM

A is a rigid cylindric hollow to be hereinafter mentioned as cup shaped body housing a bellows B and extending with a flanged opening; a wire 22 has one end clamped to the bottom B1 of the bellows B and the other end fixed to a bush 27. The wire 22 is wound, according to a feature of my invention, around a conical pulley 25. The bush 27 and the conical pulley 25 are longitudinally adjustably fixed along a vertical spindle F by means respectively of set screw $25^1$ and $27^1$. The upper end of the spindle F is formed with a platform H carrying a blood pressure recording disc L. Clearly if the pulley 25 and bush 27 are adjusted longitudinally on the spindle F a different transmission rate may be obtained; in other words the rectilinear displacements of the bellows B are adjustably transformed in the angular displacement of the spindle F. In this way a precise setting means is provided by my invention. A spring G is mounted coaxially in the bellows B to reinforce the elastic reaction of the bellows B. A bush 50 is screwed to a cover $A^1$ hereinafter mentioned as flanged frame of body A whereby a further setting means is available in that the compression of spring G can be adjusted.

Means are provided for centering the bellows B and limiting its axial deformation. For this purpose the bottom B1 of the bellows is firmly clamped to an horizontal spindle 53 the threaded portion of which is engaged by a screw set nut 54, serving as a stop. The spindle 53 slides into a cup shaped body 55 sealed to the bottom A2 of body A. It is clear that as soon as the screw set nut 54 is displaced sufficiently to engage the bottom A2 of the hollow body A a positive limitation of the contraction for the bellow is obtained. In this way the bellows B may not be damaged as a consequence of any undue contraction.

II SPRING BIASING OF THE PAPER DISC CARRYING PLATFORM AND LIMITATION OF THE MAXIMAL BLOOD PRESSURE TO BE MEASURED

The spindle F (see the FIGS. 1 and 4) is connected at its lower end to a spiral spring 28, such that when the platform H is rotated in a clockwise direction (as seen from the top of the paper disc) load on the spring increases. It is apparent that the return reaction force of spring 28 acts in contrast with the elastic stressing of bellows B (and of the related additional spring G) whereby the wire 22 is continuously in tension. The hook point 99 for the spiral spring 28 may be angularly adjusted whereby a further setting means is available.

An arm 29 is frictionally mounted on the spindle F by a friction washer 30 and a screw nut 31 (see FIG. 3). 33 is a pointer integral with the arm 29, cooperating with the graduations of the blood pressure recording disc L and carrying contact stop 34. The latter is connected (see electric wire 35) to the electric circuit.

The platform H is solid with a depending pin 60 operating as a counter-stop with the stop contact 34 so as to earth the contact 34 as soon as the same is contacted by the depending earthed pin 60.

If the maximum swinging movement of the platform L has to be limited and consequently the maximum pressure, for example 250 Mg, to be measured has to be limited, the pointer 33 is manually rotated until it centers graduation 250 of the paper disc. As soon as the earthed pin 60 comes into contact with the contact 34, the electrically operated compressor 7 is electrically disactivated whereby the invention provides a simple reliable means for the limitations the maximum pressure to be measured.

III WRITING INSTRUMENT (FIG. 1) CONTROL

An upright 36 is rigidly clamped to a bracket 66 carrying a relay N. An arm 70 carrying a pen 3 is extended by an elastic fork 38 and its upwardly directed stroke is limited by a folded portion $36^1$ of the upright 36. The pen 3 is formed with two spaced radial shoulders 69 (see FIG. 6) cooperating as a retaining means with the fork shaped portion 38 so that the pen may be easily replaced and correctly located. The pen carrying arm 70 is pivoted at 40 to a relay bracket 41 and is biased by a spring 42 urging the pen carrying arm to rotate in an anticlockwise direction (FIG. 1) away from the paper disc L, namely, in a direction opposite to that caused by the relay N.

IV AUTOMATIC CONTROL OF THE DECOMPRESSION

The automatic limiter of the measurement pressure is generally shown by the reference X and consists of an elastic membrane 1 that causes resiprocation of a needle 71 cooperating with a hole 39 in a pressurized air circuit to control the escape of pressurized air to atmosphere. When the air in the circuit is compressed the expansion of the membrane 1 moves the needle 71 to close the outflow hole 39 and prevent the escape of pressurized air to atmosphere. On the contrary, during the decompression stage caused by a not shown conventional valve, the membrane 1 returns progressively to its rest position and an ever increasing outflow of the pressurized air through the hole 39 is obtained.

V OPERATION

Once the pneumatic bracelet or cuff 9 provided with a microphone 8 has been wound around the patient's arm, the electrically operated compressor 7 is started to increase the pressure in the pressurized circuit and cause the bellows B to be compressed. This results in angular displacement of the paper disc L carrying platform H. The compressor 7 is automatically stopped when the preestablished maximum pressure for the measurement is reached as explained under heading II. The decompression step is automatically regulated by means of the automatic valve X and eventually by a not shown manual valve (see related heading IV). The microphone 8 picks up the arterial impulses that result as soon as the arterial pressure overcomes the decreasing pressure in the pneumatic bracelet and transmits the same to the electric amplifier 6. The latter transmits the signals to energize the relay N as well as a warning light SP. The energization of relay actuates the pen carrying arm 70 to cause the pen to record for each impulse a mark adjacently to the graduations of the paper disc L. The firstly marked dot shows evidently the maximum blood pressure $PM_x$ and the last marked dot shows the minimal blood pressure $PM_n$. After the measurement the paper disc may be easily removed and substituted by a fresh paper disc.

As shown the disc L is horizontally mounted upon an outside projection 90 provided with a nose 91 for cooperation and complementary aperture with a notch W formed in the disc.

What I claim is:

1. In a blood pressure recording device including a manometric bracelet or cuff adapted to encircle a limb of a person: pressure means for applying a pressure to said limb; a rotatable platform for removably supporting a blood pressure recording disc and rotating the disc in response to the value of pressure applied by said pressure means; a writing instrument for writing on said record disc and actuating means for operating said writing means to write on said record disc in response to pulse beats of blood pressure; and means for locating the said record disc with respect to the said rotatable platform, the improvement comprising the provision of a mechanism for rotating the said platform including: a cylindrical bellows having a bottom and a flanged opening; a rigid cup shaped body surrounding the said bellows; a flanged frame rigidly connected with the said cup shaped body and sealing the said flanged opening of the bellows so as to define a sealed chamber in communication with the said cuff; a first screw setting means screwed to said flanged frame; a strong cylindrical spring arranged in the said bellows and compressed between the said bottom of the said bellows and the said first screw setting means; a rotatable spindle connected to said platform, a conical pulley adjustably connected to the said spindle so as to provide a second setting means; a bush adjustably connected to the said spindle; a wire connected at one end to said bottom of the bellows and at the other end to the said bush whereby the axial deformations of the said bellows body in response to decreasing pressure in the said cuff may be adjustably converted into rotation of the said conical pulley and of the said platform; adjustable elastic means for biasing the said platform in a direction opposite to that caused by the strong cylindrical spring and constituting a third setting means.

* * * * *